United States Patent [19]

York et al.

[11] 3,997,794
[45] Dec. 14, 1976

[54] COLLIMATOR

[76] Inventors: Richard N. York, 453 Bruce Rd.;
David L. York, 100 Jefferson, both of Lockport, Ill. 60441

[22] Filed: Dec. 23, 1974

[21] Appl. No.: 536,957

[52] U.S. Cl. ............................ 250/505; 250/511
[51] Int. Cl.$^2$ ..................................... G03B 41/16
[58] Field of Search .......... 250/505, 511, 512, 513, 250/514

[56] References Cited
UNITED STATES PATENTS 2,659,017  11/1953  Bartow .............................. 250/505

*Primary Examiner*—Craig E. Church
*Attorney, Agent, or Firm*—Johnson, Dienner, Emrich & Wagner

[57] ABSTRACT

A radiation collimator having a plurality of pivotally mounted collimating tubes, with adjusting mechanism for simultaneously adjusting the tubes relative to each other to various selected positions wherein they are all focused on selected common focal points.

14 Claims, 7 Drawing Figures

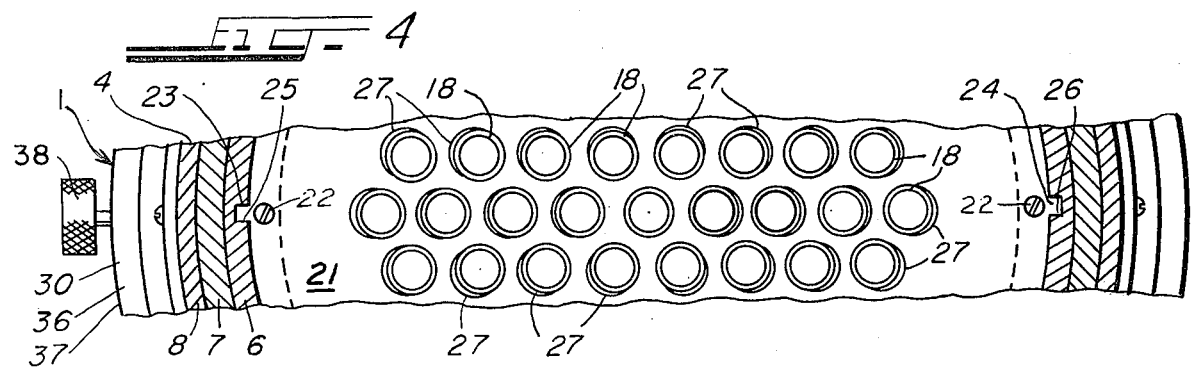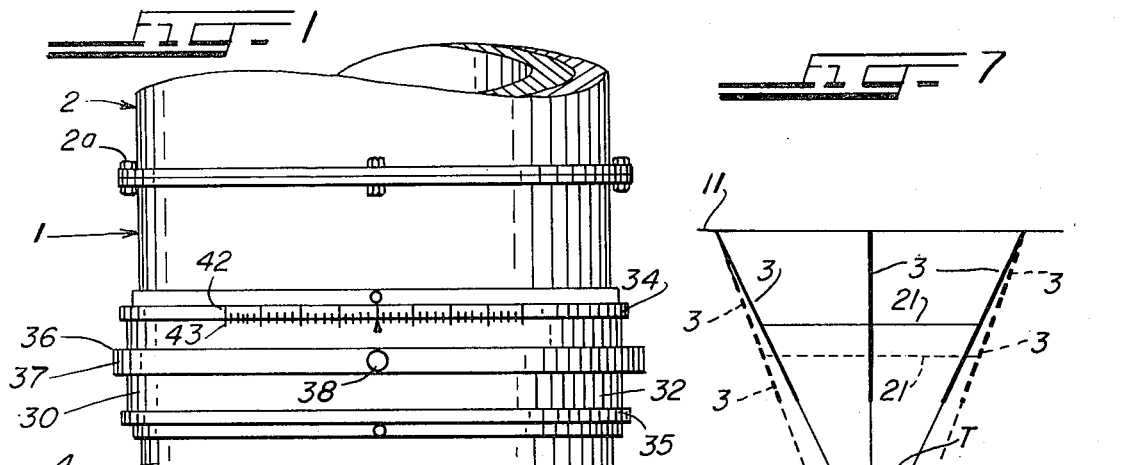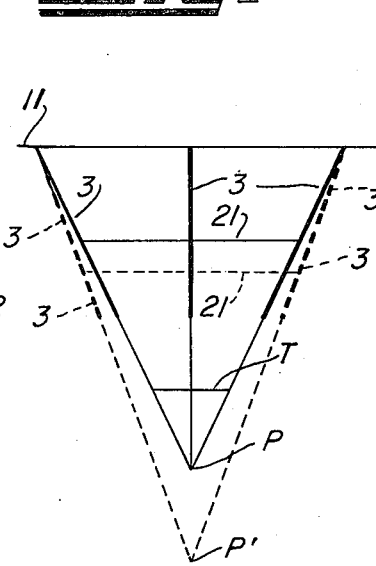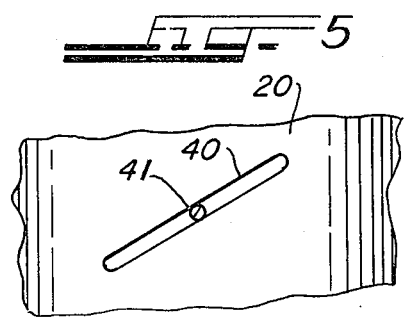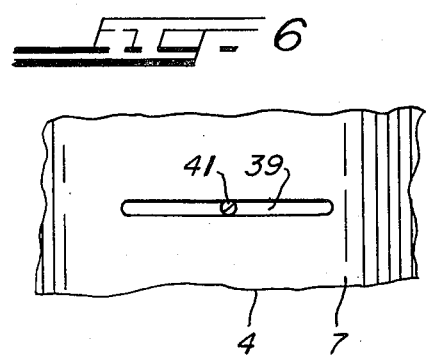

COLLIMATOR

BACKGROUND OF THE INVENTION

This invention relates to collimators, and, more particularly, to collimators which are particularly well adapted for collimating rays emanating from a source of nuclear radiation.

It is a primary object of the present invention to afford a novel collimator which is particularly well adapted for use in the nuclear radiation field.

Another object is to provide a novel collimator of the aforementioned type which is adjustable in a novel and expeditious manner.

As is well known to those skilled in the art, nuclear radiation is commonly used both for diagnostic and therapeutic purposes. For example, X-ray machines have long been used to take "pictures" of the internal structure of patients or articles being diagnosed. They have also been used for therapeutic purposes, such as, for example, to apply radiation to a selected portion of a patients body for such purposes as the treatment of cancer, and the like.

In addition, nuclear radiation has heretofore been diagnostically used by administering proper dosages of selected radiation-emanating materials to a patient to be diagnosed, and by the use of detection equipment, such as, for example, a scintillation scanner, or the like, making a study of the distribution and concentration of the administered material.

The use of nuclear radiation rays, such as, for example, X-ray and gamma rays, and the like, for both diagnostic and therapeutic purposes has posed problems relative to the control of those rays. This is particularly true where a directed beam of the rays is required, such as, for example, in the practice of therapeutic techniques wherein it is desired that the beam be concentrated on a particular surface area or at a particular focal point on or in a patient; and in the practice of diagnostic techniques, such as, for example, in those instances wherein it is desired to focus a scintillation scanner, or the like, on a radiation-emanating material disposed at a particular location in the body of a patient.

To assist in controlling nuclear radiation rays in the operation of both therapeutic and diagnostic apparatuses, collimators have long been used. Collimators heretofore known in the art for such purposes have included collimators embodying individually adjustable tubes, such as those shown in U.S. Pat. No. 2,139,966; collimators having a plurality of fixed passageways therethrough, such as shown in U.S. Pat. Nos. 3,011,057, 3,373,286 and 3,668,395; collimators having adjustable diaphrams for varying the aperture size, such as shown in U.S. Pat. Nos. 1,909,118, 2,881,329 and 2,959,680; collimators in the shape of a cone, and which are adjustable by adjusting leaves forming the sides of the cone, such as shown in U.S. Pat. Nos. 3,091,696, 3,448,270, 3,609,370 and 3,829,701; and collimators embodying tubes which are adjustable longitudinally, or channels which are adjustable by swinging them back and forth horizontally in parallel relation to each other, as shown in U.S. Pat. No. 3,790,782. It is an important object of the present invention to afford improvements over the collimators heretofore known in the art.

Another object of the present invention is to afford a novel collimator for use in the nuclear radiation field, wherein the parts thereof are so constituted and arranged that the focal point of the collimator can be varied and accurately adjusted in a novel and expeditious manner.

Another object is to afford a novel collimator of the aforementioned type, which embodies novel collimating tubes constituted and arranged in a novel and expeditious manner.

An object ancillary to the foregoing is to enable the position of all of the collimating tubes to be adjusted in a novel and expeditious manner.

A further object of the present invention is to afford a novel collimator embodying a plurality of collimating tubes, which are adjustable to various positions to thereby change the focal point of the collimator, and which collimator embodies novel mechanisms for simultaneously adjusting the positions of all of the tubes relative to each other into position to focus on the selected focal point.

Yet another object of the present invention is to afford a novel collimator embodying a plurality of adjustable collimating tubes, and wherein the tubes are held in selected adjusted positions in a novel and expeditious manner.

Another object of the present invention is to afford a novel collimator for use in the nuclear radiation field, which is practical and efficient in operation, and which may be readily and and economically produced commercially.

Other and further objects of the present invention will be apparent from the following description and claims and are illustrated in the accompanying drawings which, by way of illustration, show a preferred embodiment of the present invention and the principles thereof and what we now consider to be the best mode in which we have contemplated applying these principles. Other embodiments of the invention embodying the same or equivalent principles may be used and structural changes may be made as desired by those skilled in the art without departing from the present invention and purview of the appended claims.

DESCRIPTION OF THE DRAWINGS

In the drawings:

FIG. 1 is an elevational view of a collimator embodying the principles of the invention, showing the collimator attached to apparatus with which it is intended to operate;

FIG. 4 is a fragmentary, detail sectional view taken substantially along the line 4—4 in FIG. 2;

FIG. 5 is a fragmentary, detail sectional view taken substantially along the line 5—5 in FIG. 2;

FIG. 6 is a fragmentary, detail sectional view taken substantially along the line 6—6 in FIG. 2; and FIG. 7 is a diagramatic illustration of the manner in which the focal point of the collimator shown in FIG. 1 may be adjusted.

DESCRIPTION OF THE EMBODIMENT SHOWN HEREIN

Figure 2:
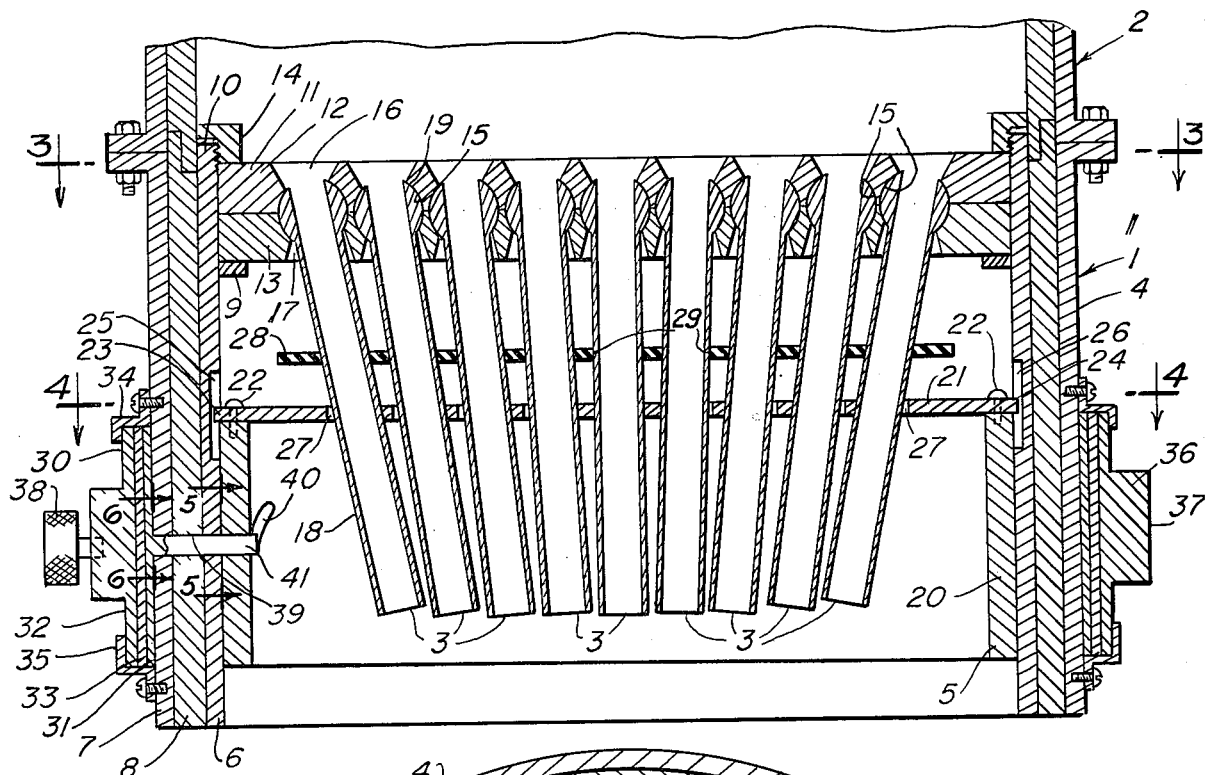
FIG. 2 is a longitudinal sectional view taken substantially along the line 2—2 in FIG. 1.
Figure 3:
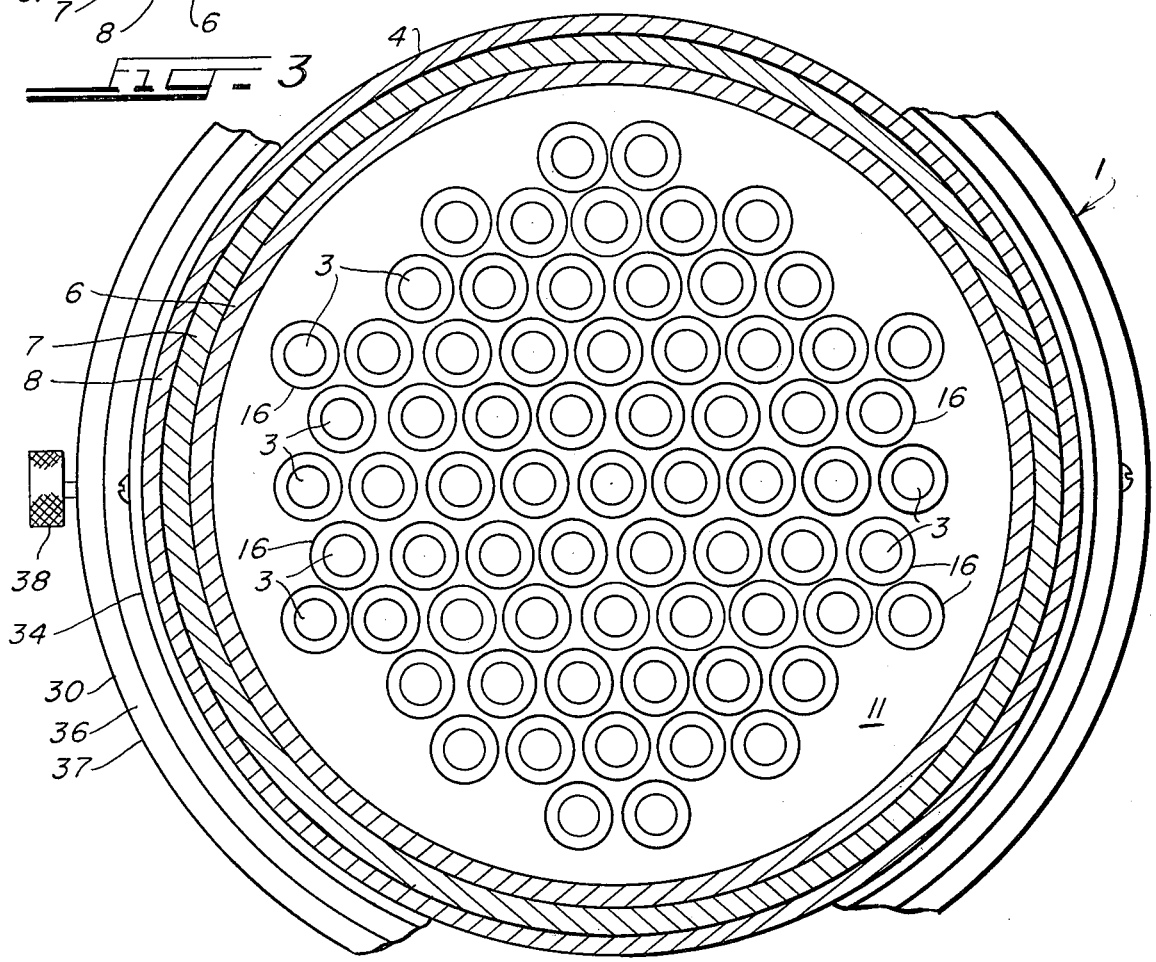
FIG. 3 is a fragmentary, detail sectional view taken substantially along the line 3—3 in FIG. 2.

A collimator 1, embodying the principles of the present invention, is shown in the drawings to illustrate the presently preferred embodiment of the present invention.

The invention will be described herein with respect to the collimator 1 being used in apparatus used in diagnostic procedures, wherein the rays to be collimated emanate from a source external to the apparatus and pass from the source, through the collimator and into the apparatus. However, as will be appreciated by those skilled in the art, this is merely by way of illustration and not by way of limitation, and the collimator 1 may be used, without departing from the purview of the broader aspects of the present invention, with other apparatus, such as, for example, with apparatus used in therapeutic or diagnostic procedures, wherein the rays to be collimated emanate from within the apparatus, and pass from the apparatus, through the collimator to a target area, such as, for example, a portion of a body which is to be treated by radiation, or a portion of a body of which an X-ray picture is to be taken, respectively.

Thus, a collimator 1 is shown in the drawings mounted on apparatus 2, which for the purposes of the present invention may be considered to be a detector, such as, for example, a scintillation scanner. The collimator 1 may be attached to the apparatus 2 by any suitable means such as screws or bolts 2a, FIGS. 1 and 2, and embodies, in general, a plurality of radiation-confining tubes 3, FIG. 2, movably mounted in a substantially tubular shaped radiation-confining shell or housing 4, with adjusting mechanism 5 operatively mounted on and in the shell 4 for adjusting the position of the tubes 3, as will be discussed in greater detail hereinafter.

The shell 4, FIG. 2, embodies an inner tubular sleeve 6 and an outer tubular sleeve 7, which may be made of any suitable wear resistant material, such as, for example, steel, with an intermediate tubular sleeve 8, which may be made of any suitable radiation-absorbing material, such as, for example, lead alloy or tungsten, or the like, disposed between the sleeves 6 and 7 and suitably secured thereto, such as, for example, by soldering. The sleeve 8 extends the full length of the sleeves 6 and 7 and is disposed in encircling relation to the inner sleeve 6.

The shell 4 is round in transverse cross section, and embodies a ring 9 mounted in the inner sleeve 6 in downwardly spaced relation to the upper end 10 of the latter. The ring 9 may be made of any suitable material, such as, for example, steel and is attached to the sleeve 6 by suitable means, such as, for example, by welding.

A supporting plate 11, which may be made of any suitable radiation-absorbing material, such as the aforementioned lead alloy or tungsten, is disposed in the upper end portion of the sleeve 6 and rests on the ring 9. The supporting plate 11 is round in transverse cross section and, preferably, is of such size that it is disposed in the inner sleeve 6 with a relatively snug, but freely slidable fit. It embodies an upper plate 12 and a lower plate 13 disposed in flat, juxtaposition to each other, with the lower face of the lower plate 13 resting on the ring 9, and with the upper face of the upper plate 12 disposed in downwardly spaced relation to the upper end 10 of the inner sleeve 6. The upper end portion of the inner sleeve 6 is internally threaded and an annular nut 14 is threadedly engaged therein and, in the assembled collimator 1, is disposed in abutting engagement with the upper face of the supporting plate 11 in position to firmly clamp the supporting plate 11 against the ring 9. The nut 14 also overlies the upper end of the inner sleeve 6 in spaced relation thereto, and is made of a suitable radiation-absorbing material, such as, for example, the aforementioned lead alloy or tungsten.

The supporting plate 11 embodies a plurality of substantially spherical-shaped, internal cavities or openings 15 disposed at the junction of the upper plate 12 and the lower plate 13, with one-half of each of the openings 15 being disposed in each of the plates 12 and 13. Each of the openings 15 is disposed between, and in communication with, an upwardly and outwardly flaring opening 16 in the upper portion of the upper plate 12, and a downwardly and outwardly flaring opening 17 in the lower portion of the lower plate 13, FIG. 2, each respective pair of openings 16 and 17 being disposed in axial alignment with each other.

Each of the tubes 3 embodies an elongated, substantially straight body portion 18 having a substantially spherical-shaped upper end portion 19, FIG. 2. The body portion 18 of each of the tubes 3, below the end portion 19, preferably is round in transverse cross section and substantially constant in internal and external diameter. Each of the tubes 3 is made of a suitable radiation absorbing material, such as, for example, the aforementioned lead alloy or tungsten, or the like, and, if desired, may embody an outer coating or shell, not shown, of a suitable wear resistant material, such as, for example, steel.

In the assembled collimator 1, the tubes 3 are supported by the supporting plate 11 in suspended relation thereto, with the upper ends 19 disposed in respective ones of the openings 15, and with the body portions 18 projecting downwardly through respective ones of the lower openings 17 in the supporting plate 11. The end portions 19 of the tubes 3 preferably are of such size and shape that they engage the internal surfaces of the supporting plate 11, which define the respective openings 15 therein, with a relatively snug, but freely rotatable-sliding fit.

The adjusting mechanism 5 embodies a sleeve 20 which is mounted in the inner sleeve 6 of the shell 4. The sleeve 20 is round in transverse cross section and preferably is of such size that it engages the inner face of the sleeve 6 with a relatively snug, but freely-slidable fit. The sleeve 20 may be made of any suitable material, such as, for example, steel.

An adjusting plate 21 is mounted on the upper end of the sleeve 20 and is secured thereto by suitable means, such as, for example, screws or bolts 22. The adjusting plate 21 is round in transverse cross section and is disposed in the sleeve 6 with a relatively snug, but freely-slidable fit. Two ears 23 and 24 project outwardly from diametrically opposite sides of the adjusting plate 21, FIGS. 2 and 4, and are disposed in vertically extending slots 25 and 26, respectively, formed in the inner face of the inner sleeve 6, with a relatively snug, but freely slidable fit.

The adjusting plate 21 has a plurality of openings 27 extending vertically therethrough, FIGS. 2 and 4. The openings 27 correspond in number to the openings 15–17 extending through the supporting plate 11, and in the assembled collimator 1, each of the body portions 18 of the tubes 3 extend downwardly through a respective one of the openings 27. The central one of the openings 27 preferably is round in transverse cross section, and is of such size that the central tubular member 3 extending therethrough is disposed therein with a relatively snug, but freely slidable fit. The openings 15–17 and 27 within which the central one of the tubes 3 is disposed are so disposed relative to each other that the central tube 3 is, at all times, so positioned in the collimator 1 that it extends along the longitudinal axis of the shell 4.

All of the other openings 27, which are disposed outwardly of the aforementioned central openings 27, are disposed in such position in the adjusting plate 21, that the tubes 3, which extend therethrough, slope inwardly, from top to bottom, toward the longitudinal axes of the shell 4 and of the central one of the tubes 3. All of these outer openings 27 are elongated in a radial direction relative to the aforementioned central opening 27, FIG. 4, and preferably are of such lateral width that the tubes 3 which project therethrough are disposed between the lateral sides thereof with a relatively snug, but freely-slidable fit. The radially inner ends of the elongated outer openings 27 are so positioned in the adjusting plate 11 that, when the body portions 18 of the tubes 3 extending through the outer openings 27 are disposed in abutting engagement with the portions of the plate 11 defining the inner ends of the openings 27, all of the tubes 27 are focused on a common focal point spaced downwardly below the shell 4 on the longitudinal axis of the latter.

A holding plate or retainer plate 28, FIG. 2 is disposed between the supporting plate 11 and the adjusting plate 21. The holding plate 28 has a plurality of openings 29 extending therethrough, corresponding in number to the openings 27 extending through the adjusting plate 21, and, in the assembled collimator 1, the body portions 18 of the tubes 3 extend through respective ones of the openings 29 in the holding plate 28.

The holding plate 28 is made of a suitable, resilient material, such as, for example, foam rubber, and the openings 29 therein are of such size that the body portions 18 of the respective tubes 3 extending therethrough are disposed therein with a relatively snug fit, effective to frictionally hold the holding plate 28 against vertical movement longitudinally of the tubes 3. The central one of the openings 29 is disposed in axial alignment with the central one of the openings 15–17 in the supporting plate 11 and the central one of the openings 27 in the adjusting plate 21. The other ones of the openings 29 in the holding plate 28 are disposed in such position that they engage the body portions 18 of the respective tubes 3 extending therethrough in such a manner as to yieldingly urge the respective tubes 3 radially inwardly into abutting engagement with the aforementioned radially inner ends of the respective openings 27 in the adjusting plate 21 through which the tubes 3 extends, to thereby yieldingly hold all of the tubes 3 focused on a common focal point.

It will be seen that, with this construction, downward and upward movement of the adjusting plate 21 is effective to cause all of the tubes 3, with the exception of the central one of the tubes 3, to swing outwardly and inwardly, respectively, around their upper end portions 15 relative to each other along paths of movement extending radially from the longitudinal axis of the shell 4 and of the central tube 3, the holding plate 28, in all positions of the adjusting plate 21 being effective to yieldingly hold the respective tubes 3, outwardly of the central tube 3, in engagement with the radial inner ends of the openings 27 through which they extend. Thus, in the assembled collimator 1, by vertically adjusting the position of the adjusting plate 21, the focal point of the collimator 1 may be adjusted, as will be discussed in greater detail presently.

The adjusting mechanism 5 also includes an annual collar 30 extending around the shell 4 in radially outwardly disposed relation to the sleeve 20, FIG. 2. The collar 30 embodies an inner annular member 31 and an outer annular member 32, with an intermediate annular member 33 disposed between the members 31 and 32. The inner member 31 and the outer member 32 preferably are made from suitable wear-resistant material, such as, for example, steel, and the intermediate member 33 may be made of a suitable radiation-absorbing material, such as, for example, the aforementioned lead alloy or tungsten.

The collar 30 is round in transverse cross-section, and preferably is of such size that it engages the outer face of the outer sleeve 7 of the shell 4 with a relatively snug, but manually slidable frictional fit. It is rotatably mounted on the shell 4 and is disposed between two mounting rings 34 and 35, FIG. 2, which are effective to hold the collar 30 against displacement longitudinally of the shell 4.

An annular projection 36, projects outwardly from the central portion of the outer annular member 32 of the collar 30, and the radially outer face 37 of the projection 36 preferably is roughened, such as, for example, by knurling, not shown, so that an operator, by engaging his fingers with the surface 37, may readily turn the collar 30 around the shell 4. In the preferred form of the collimator 1 shown in the drawings, a handle 38 also is mounted in the projection 36 and projects outwardly therefrom, FIGS. 1 and 2, so that, if desired, the handle 38 may be grasped in the fingers of an operator for rotating the collar 30 around the shell 4.

A substantially straight, elongated slot 39 extends through the sleeves 6–8 of the shell 4, in substantially perpendicular relation to the longitudinal axis of the shell 4, FIG. 6. Another elongated, substantially straight slot 40, FIGS. 2 and 5, extends through the sidewall of the sleeve 20, which is disposed adjacent to the opening 39, the plane of the opening 40 being disposed at a suitable vertical angle, such as, for example, thirty degrees, to the horizontal plane of the slot 39, for a purpose which will be discussed in greater detail presently.

A pin or projection 41, which is integral with or otherwise suitably secured to the inner annular member 31 of the collar 30, FIG. 2, projects inwardly therefrom through the slots 39 and 40. The pin 41 preferably is of such transverse cross-sectional size that it is disposed between the lateral sides of the slots 39 and 40 with a relatively snug, but freely slidable fit.

It will be seen that, with this construction of the collimator 1, rotation of the collar 30 around the sleeve 4 is effective to move the pin 41 longitudinally of the slots 39 and 40; and with the slot 40 disposed at the angle shown in FIG. 5, movement of the collar 30 to the right, as viewed in FIG. 1 and 2, is effective to cam the sleeve 20 of the adjusting mechanism 5 downwardly, and movement of the collar 30 to the left, as viewed in FIGS. 1 and 2, is effective to move the sleeve 20 upwardly. If desired, suitable indicia, such as, for example, suitable scales, such as the scales 42 and 43, FIG. 1, may be disposed on suitable portions of the collimator 1, such as on the ring 34 and the collar 30, respectively, for indicating the adjusted position of the collar 30 relative thereto, and thus indicating the vertically adjusted position of the sleeve 20 and the adjusting plate 21 carried thereby.

It will be seen that with the collimator 1 constructed in the aforementioned manner, an operator, by rotating the collar 30 around its longitudinal axis, can adjust the position of the sleeve 20 longitudinally of the shell 4, and thereby adjust the focal point of the collimator 1. It will be remembered that the openings 15–17 in the supporting plate 12, the openings 29 in the holding plate 28 and the openings 27 in the adjusting plate 21 are so constituted and arranged relative to each other that, in all adjusted positions of the adjusting plate 21, all of the tubes 3 are focused on a common focal point. Thus, for example, to adjust the focal point P downwardly to another focal point P', as illustrated diagramatically in FIG. 7, the collar 30 may be turned to the right, as viewed in FIGS. 1 and 2, to thereby cause the pin 41 to move to the right along the slot 40 in the sleeve 20, FIG. 5, and thus cause the sleeve 20 and the adjusting plate 21 carried thereby, to move downwardly from the position shown in solid lines in FIG. 7 to the position shown in broken lines in FIG. 7. Such downward movement of the adjusting plate 21 is effective, through the engagement of the inner ends of the openings 27 with the body portion 18 of the tubes 3, disposed outwardly of the central tube 3, to swing the aforementioned outwardly disposed tubes 3 radially, relative to the central tube 3 into a position, outwardly, such as that shown in broken lines in FIG. 7, to thereby focus the tubes 3 on the new, lower focal point P'. Conversely, movement of the collar 30 to the left, as viewed in FIG. 1, around the shell 4 is effective, by reason of the movement of the pin 41 to the left along the slot 40, to cause the sleeve 20 to be raised, and thus raise the actuating plate 21 from a lower position such as shown in broken lines in FIG. 7 to a raised position, such as shown in solid lines in FIG. 7, to thereby free the tubes 3, disposed outwardly to the center tube 3, for inward movement relative to the latter, by reason of the urging of the holding plate 28 and thus focus all of the tubes 3 on a higher focal point, such as the focal point P shown in FIG. 7.

In some instances it may be desired to focus the tubes 3 on a target area, such as the target area T indicated in FIG. 7. This is particularly true in those instances wherein the collimator 1 is being used with therapeutic apparatus, by means of which it is desired to irradiate a particularly defined area, such as the target area T. It will be seen that the collimator 1 may be effectively focused on such areas, in the same manner as it may be focused on focal points, as previously described.

During the aforementioned movement of the adjusting plate 21 longitudinally of the shell 4, the ears 23 and 24 thereon, slide upwardly and downwardly along the slots 25 and 26, respectively, and by reason of the snug, frictional fit of the ears 23 and 24 in the slots 25 and 26, the adjusting plate 21 is effectively held against rotation relative to the shell 4.

Also, it will be seen that the radially-elongated construction of the openings 27 in the adjusting plate 21 affords clearance for the radial swinging movement of the body portions 18 of the tubes 3 therein, during such adjustment of the focal point of the collimator 1, the holding plate 21 being effective to yieldingly hold the tubes 3, disposed outwardly of the central tube 3, in engagement with the inner ends of the respective openings 27, at all times.

In addition, it will be seen that the outwardly flaring construction of the upper opening 16 and lower opening 17 in the supporting plate 11 enables the tubes 3 to be aligned with respective internal portions of the apparatus 2 without interference from the supporting plate 11, in all positions of the tubes 3 relative to each other. Also, the outward flaring of the lower openings 17 in the supporting plate 11 enables the tubes 3, which are disposed outwardly of the center tube 3, to be swung into their various adjusted positions without obstructing engagement with the supporting plate 11.

In the preferred form of the collimator 1 shown in the drawings, the frictional engagement of the collar 30 with the outer face of the shell 4 is relied upon to hold the collar 30 in properly adjusted position relative to the shell 4. However, as will be appreciated by those skilled in the art, other means for holding the collar 30 in adjusted position, such as, for example, a suitable clamping member, not shown, may be utilized, if desired, without parting from the purview of the broader aspects of the present invention.

Also, as will be appreciated by those skilled in the art that, although in the preferred form of the present invention, illustrated by the collimator 1 shown in the drawings, the tubes 3 are so disposed therein that they may be focused on a common focal point disposed below the supporting plate 11 as viewed in FIGS. 1 and 2, this is merely by way of illustration, and not by way of limitation, and, if desired, the openings 15–17, 27 and 29 may be so disposed relative to each other that the tubes 3 may be focused on a point disposed above the supporting plate 11, as viewed in FIGS. 1 and 2, without departing from the purview of the broader aspects of the present invention.

From the foregoing, it will be seen that the present invention affords a novel collimator.

Also, it will be seen that the present invention affords a novel collimator having individual collimating passageways afforded therethrough, and which passageways may be adjusted relative to each other in a novel and expeditious manner.

In addition, it will be seen that the present invention affords a novel collimator wherein the focal point thereof may be readily adjusted in a novel and expeditious manner.

Also, it will be seen that the present invention affords a novel collimator which is practical and efficient in operation, and which may be readily and economically produced commercially.

Thus, while we have illustrated and described the preferred embodiment of our invention, it is to be understood that this is capable of variation and modification, and we therefore do not wish to be limited to the precise details set forth, but desire to avail ourselves of such changes and alterations as fall within the purview of the following claims.

We claim:
1. A radiation collimator comprising
   a. a radiation-absorbing tubular housing,
   b. a radiation-absorbing supporting plate mounted in said housing and extending transversely thereacross,
   c. said plate having a plurality of substantially spherical-shaped cavities therein,
   d. a plurality of elongated, substantially straight radiation-absorbing collimating tubes having
      1. elongated body portions, and
      2. substantially spherical-shaped end portions on one end of said body portions,
   e. said end portions being disposed in respective ones of said cavities for pivotally supporting said tubes from said plate, f. one of said tubes projecting from said plate along the longitudinal axis of said housing, g. the other of said tubes projecting from said plate at an acute angle toward said longitudinal axis of said housing in position to align longitudinal axes of said other tubes with a common point on said longitudinal axis of said housing, h. another plate
 1. having a plurality of openings therethrough, and
 2. slidably mounted in said housing for movement longitudinally thereof, i. said body portions extending through respective openings in said other plate, and j. means mounted on the outside of said housing and operatively connected to said other plate for moving said other plate along said first mentioned tubes longitudinally of said housing and thereby swinging said other tubes radially relative to said longitudinal center line of said housing for aligning the longitudinal axes of said other tubes with selected common points along said longitudinal axis of said housing corresponding to the positions of said other plate longitudinally of said housing.

2. A collimator comprising
a. a plurality of collimating tubes,
b. means for supporting said tubes for swinging movement relative to each other, and
c. means for simultaneously adjusting the relative position of all of said tubes relative to each other,
d. said second mentioned means comprising a plate
 1. disposed between the ends of said tubes,
 2. through which said tubes extend, and
 3. which is movable longitudinally of said tubes.

3. A collimator comprising
a. a plurality of collimating tubes,
b. means for supporting said tubes for swinging movement relative to each other, and
c. means for simultaneously adjusting the relative position of all of said tubes relative to each other
d. said second mentioned means comprising a plate
 1. through which said tubes extend, and
 2. which is movable longitudinally of said tubes,
e. said second mentioned means including resilient means for yieldingly holding said tubes in one position relative to said plate.

4. A collimator comprising
a. a plurality of collimating tubes,
b. means for supporting said tubes for swinging movement relative to each other, and
c. means for simultaneously adjusting the relative position of all of said tubes relative to each other,
d. said tubes comprising substantially straight elongated members having
 1. a substantially spherical-shaped end portion, and
 2. an elongated body portion extending from said end portion,
e. said supporting means having a plurality of substantially spherical-shaped openings therein which are substantially complementary in size and shape to said end portions,
f. said end portions being disposed in respective ones of said openings, and
g. said adjusting means comprising
 1. a plate
   a. having a plurality of openings therethrough and through respective ones of which respective ones of said body portions extend, and
   b. which is movable between the ends of said tubes longitudinally of said tubes, and
 2. resilient means extending around and operatively engaged with said body portions in position to yieldingly hold said body portions in engagement with predetermined portions of said plate.

5. A collimator as defined in claim 4, and in which
a. said movement of said plate to selected positions longitudinally of said tubes is effective to align all of said tubes with respective portions of target areas corresponding to said selected positions.

6. A radiation collimator comprising
a. a plurality of radiation-absorbing elongated tubes,
b. means for supporting said tubes for swinging movement relative to each other, and
c. means for simultaneously adjusting all of said tubes relative to each other into various positions wherein they are all aligned with a respective common focal point,
d. said means for adjusting comprising
 1. abutment means movable longitudinally of said tubes into abutting engagement with said tubes at selected positions longitudinally of said tubes, and
 2. resilient means for yieldingly holding said tubes and abutment means in said abutting engagement.

7. A radiation collimator comprising
a. a radiation-absorbing tubular housing,
b. a radiation-absorbing supporting plate mounted in said housing and extending transversely thereacross,
c. a plurality of elongated, substantially straight radiation-absorbing tubes pivotally mounted in said plate in outwardly projecting relation thereto,
d. said tubes projecting from said plate in such directions that the axial center lines thereof converge at a common point,
e. means movably mounted in said housing for movement longitudinally thereof,
f. said means being engaged with said tubes between the ends thereof at such position that movement of said means longitudinally of said housing in a direction away from said plate is effective to pivot at least certain of said tubes outwardly away from each other into positions wherein the axial center lines thereof converge on a common point different from said first mentioned point, and
g. other means engaged with said tubes and yieldingly urging the latter in a direction effective to maintain said engagement of said first mentioned means with said tubes at said first mentioned position.

8. A radiation collimator as defined in claim 7, and in which
a. said tubes have
 1. one end portion pivotally attached to said plate, and
 2. elongated body portions extending from respective ones of said end portions,
b. said other means comprises a yieldable resilient plate having openings therein, and
c. said body portions are disposed in said openings with a frictional fit.

9. A radiation collimator as defined in claim 7, and in which
a. said tubes comprise
 1. elongated body portions, and
 2. substantially spherical-shaped end portions on one end of said body portions, and
b. said end portions are disposed in substantially complementary shaped cavities in said plate.

10. A radiation collimator comprising
  a. a radiation-absorbing tubular housing,
  b. a radiation-absorbing supporting plate mounted in said housing and extending transversely thereacross,
  c. a plurality of elongated, substantially straight radiation-absorbing tubes pivotally mounted in said plate in outwardly projecting relation thereto,
  d. said tubes projecting from said plate in such directions that the axial center lines thereof converge at a common point,
  e. means movably mounted in said housing for movement longitudinally thereof,
  f. said means being engaged with said tubes at such position that movement of said means longitudinally of said housing in a direction away from said plate is effective to pivot at least certain of said tubes outwardly away from each other into positions wherein the axial center lines thereof converge on a common point different from said first mentioned point, and
  g. other means engaged with said tubes and yieldingly urging the latter in a direction effective to maintain said engagement of said first mentioned means with said tubes at said first mentioned position,
  h. said tubes having
    1. one end portion pivotally attached to said plate, and
    2. elongated body portions extending from respective ones of said end portions,
  i. said first mentioned means comprising a plate having a plurality of openings therethrough,
  j. said body portions extending through respective ones of said openings,
  k. at least the openings through which said body portions of said certain tubes extend being elongated in the direction of said pivotal movement of said certain tubes, and
  l. said position on said first mentioned means comprising the portion of said plate defining the ends of said openings disposed at the side of said certain tubes remote from the direction that said certain tubes move outwardly away from each other.

11. A radiation collimator as defined in claim 10, and in which
  a. said other means comprises a yieldable resilient plate having openings therein, and
  b. said body portions are disposed in said openings with a frictional fit.

12. A radiation collimator as defined in claim 11, and in which
  a. said first mentioned means includes a sleeve movably mounted in said housing for movement longitudinally thereof, and
  b. said plate of said first mentioned means is mounted on and carried by said sleeve.

13. A radiation collimator as defined in claim 12, and in which
  a. said one end portions of said tubes
    1. are substantially spherical in shape, and
    2. are disposed in substantially complementary shaped internal cavities in said first mentioned plate,
  b. said first mentioned plate has a pair of axially aligned outwardly tapering elongated openings projecting outwardly from opposite sides of respective ones of each of said cavities, and
  c. said body portion of each of said tubes extends through a respective one of said last mentioned openings.

14. A radiation collimator as defined in claim 12, and in which
  a. said housing has a substantially straight elongated slot extending therethrough and disposed in a plane which is substantially perpendicular to the longitudinal axis of said housing,
  b. said sleeve has an elongated slot therethrough and extending at an acute angle to said plane of said first mentioned slot,
  c. a radiation-absorbing collar is rotatably mounted on said housing in radially outwardly disposed relation to said sleeve and said slots for rotation around said housing, and
  d. a pin carried by said collar is disposed in said slots in position to cam said sleeve longitudinally of said housing upon rotation of said collar around the latter.

* * * * *